United States Patent
McGee

(10) Patent No.: US 11,045,637 B2
(45) Date of Patent: Jun. 29, 2021

(54) COLOR-CODED ROLLER CLAMP APPARATUS

(71) Applicant: Leslie McGee, Fairfield, CA (US)

(72) Inventor: Leslie McGee, Fairfield, CA (US)

( * ) Notice: Subject to any disclaimer, the term of this patent is extended or adjusted under 35 U.S.C. 154(b) by 69 days.

(21) Appl. No.: 16/528,770

(22) Filed: Aug. 1, 2019

(65) Prior Publication Data

US 2021/0031025 A1 Feb. 4, 2021

(51) Int. Cl.
*A61M 39/28* (2006.01)
*F16K 37/00* (2006.01)
*A61M 5/168* (2006.01)

(52) U.S. Cl.
CPC ...... *A61M 39/286* (2013.01); *A61M 5/16813* (2013.01); *A61M 5/16881* (2013.01); *A61M 39/287* (2013.01); *F16K 37/0058* (2013.01); *A61M 2205/584* (2013.01)

(58) Field of Classification Search
USPC ......................................................... 251/4, 6
See application file for complete search history.

(56) References Cited

U.S. PATENT DOCUMENTS

| | | | |
|---|---|---|---|
| D230,729 S | 3/1974 | Al Zeddies | |
| 3,915,167 A | 10/1975 | Waterman | |
| 4,406,440 A * | 9/1983 | Kulle | A61M 39/286 251/6 |
| 4,725,037 A * | 2/1988 | Adelberg | A61M 39/286 251/6 |
| 4,895,340 A * | 1/1990 | Forberg | A61M 39/286 251/6 |
| 5,088,990 A | 2/1992 | Hivale | |
| 6,406,426 B1 | 6/2002 | Reuss | |
| 8,486,019 B2 | 7/2013 | White | |
| 9,308,323 B2 | 4/2016 | Adams | |
| 10,072,959 B2 | 9/2018 | Bochenko | |
| 2012/0283630 A1 | 11/2012 | Lee | |

FOREIGN PATENT DOCUMENTS

CN 108114340 A * 6/2018

OTHER PUBLICATIONS

CN108114340A1, Machine Translation, 2018 (Year: 2018).*

* cited by examiner

*Primary Examiner* — Daphne M Barry

(57) ABSTRACT

A color-coded roller clamp apparatus for easily clamping an IV tube includes a clamp housing having a clamp inside. A top aperture and a roller slot extend through to the clamp inside. The clamp housing is configured to receive an IV tube passing through the top aperture and out a bottom. A roller is coupled to the clamp housing and comprises a wheel partially extending through the roller slot. A first hemisphere and a second are a first color and a second color, respectively. An axle is coupled to the wheel within the clamp. The roller is rollingly moveable between a disengaged position alternative engaged. The wheel in the disengaged position exposes the first hemisphere through the roller slot and the wheel in the engaged position exposes the second hemisphere through the roller slot and is configured to clamp the IV tube against the back side to prevent flow.

8 Claims, 5 Drawing Sheets

COLOR-CODED ROLLER CLAMP APPARATUS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to tube clamps and more particularly pertains to a new tube clamp for easily clamping an IV tube.

(2) Description of Related Art Including Information Disclosed Under 37 CFR 1.97 and 1.98

The prior art relates to tube clamps.

BRIEF SUMMARY OF THE INVENTION

An embodiment of the disclosure meets the needs presented above by generally comprising a clamp housing having a front side, a back side, a left side, a right side, a top side, and a bottom side defining a clamp inside. A top aperture extends through the top side to the clamp inside. A roller slot extends through the front side to the clamp inside from proximal the top side to proximal the bottom side. The back side has a raised medial portion and a pair of lateral portions. The bottom side has a bottom aperture extending through the medial portion. The clamp housing is configured to receive an IV tube passing through the top aperture and out the bottom aperture along the medial portion. A roller is coupled to the clamp housing and comprises a wheel having a left face, a right face, and a perimeter face. The wheel partially extends through the roller slot. A first hemisphere and a second hemisphere of each of the left face, the right face, and the perimeter face are a first color and a second color, respectively. An axle is coupled to the wheel. The axle centrally extends through each of the left face and the right face. The axle is coupled within the clamp inside between the front side and the pair of lateral portions of the back side. The roller is rollingly moveable between a disengaged position proximal the top side and an alternative engaged position proximal the bottom side. The wheel in the disengaged position exposes the first hemisphere through the roller slot and the wheel in the engaged position exposes the second hemisphere through the roller slot and is configured to clamp the IV tube against the back side to prevent flow.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
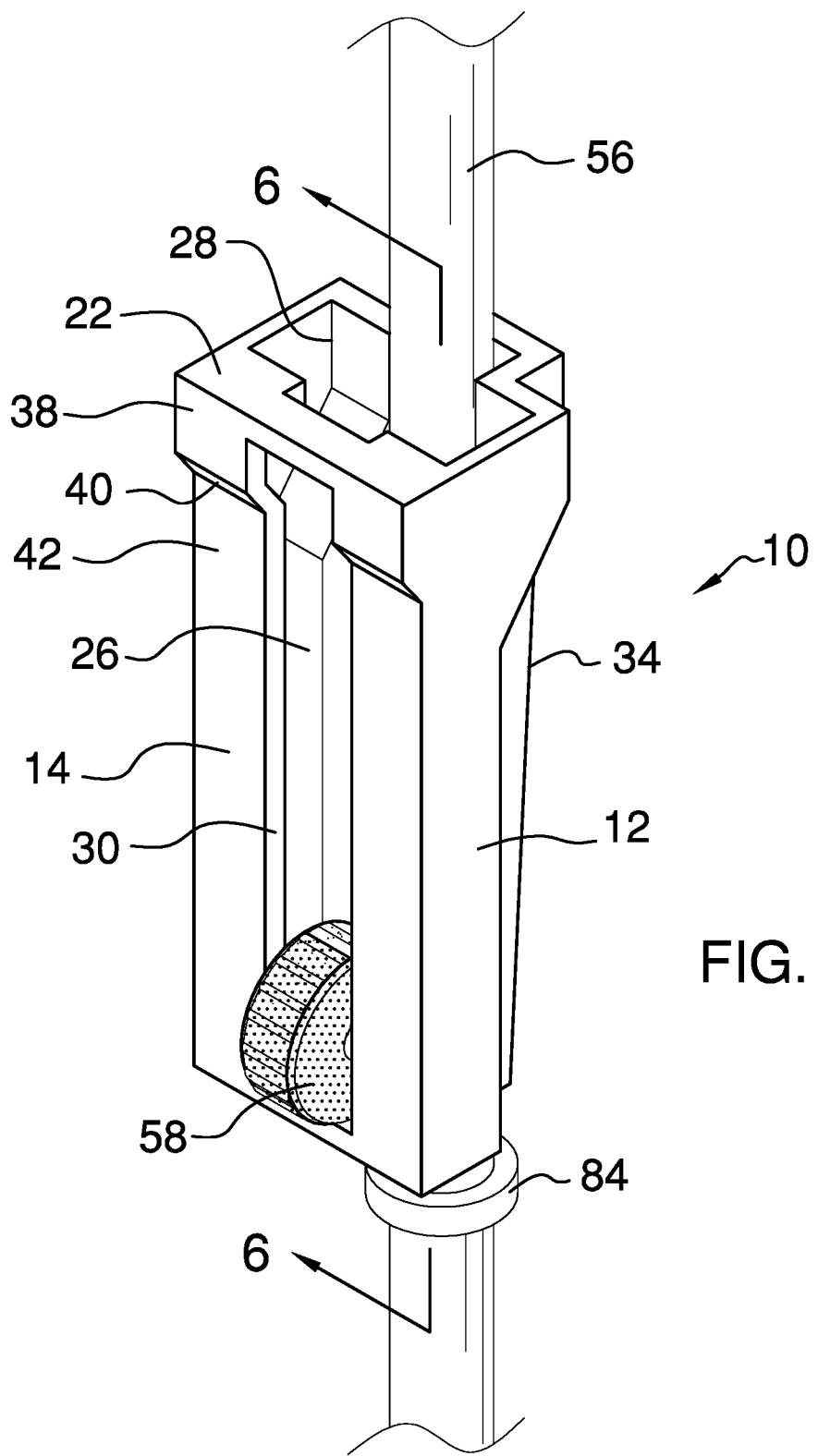
FIG. 1 is an isometric view of a color-coded roller clamp apparatus according to an embodiment of the disclosure.
Figure 2:
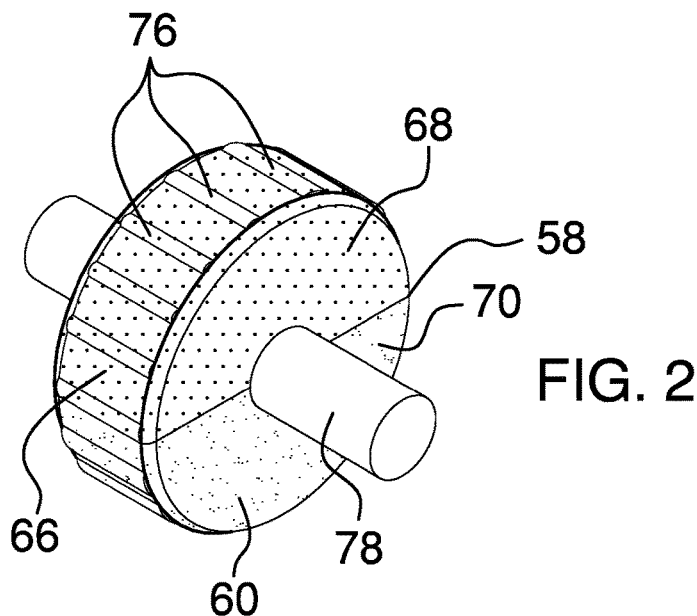
FIG. 2 is an isometric view of an embodiment of the disclosure.
Figure 3:
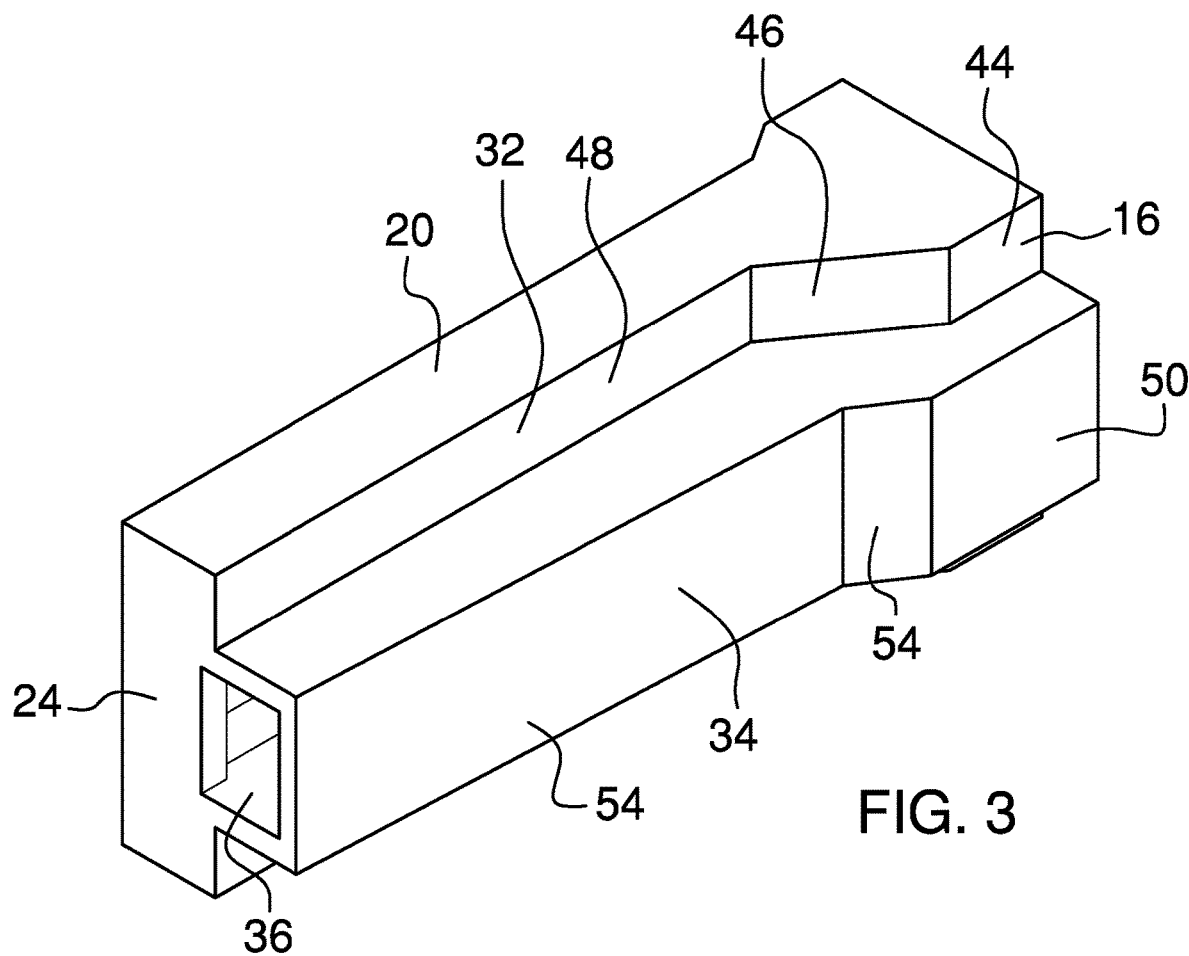
FIG. 3 is an isometric view of an embodiment of the disclosure.
Figure 4:
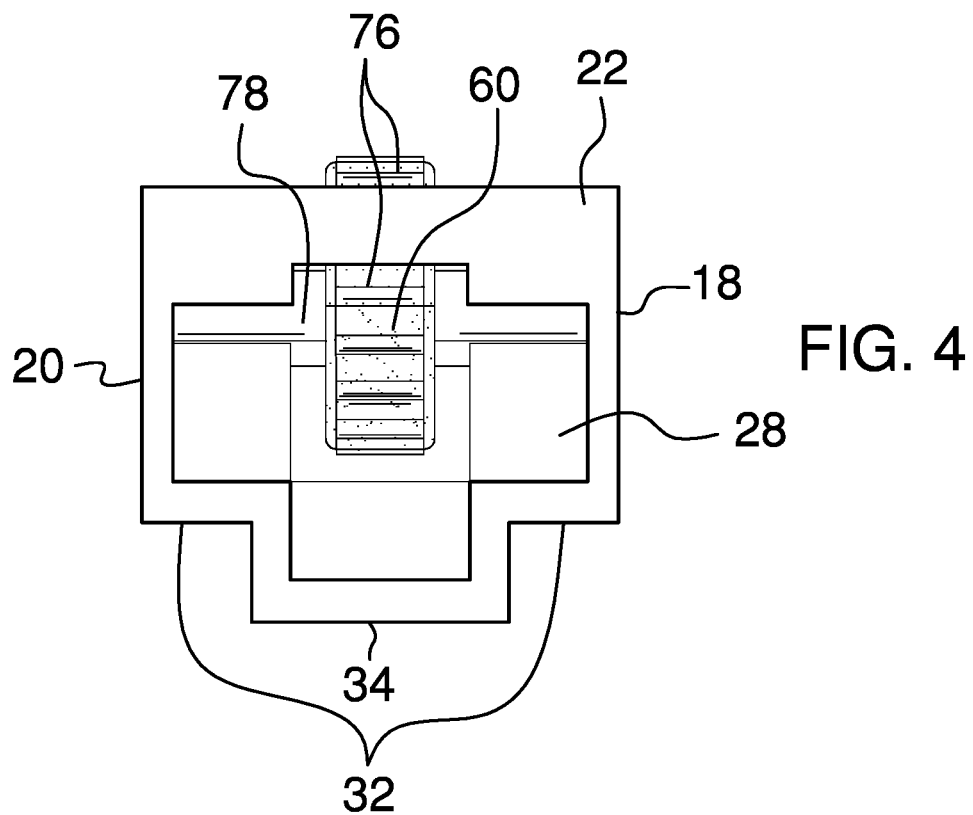
FIG. 4 is a front elevation view of an embodiment of the disclosure.
Figure 5:
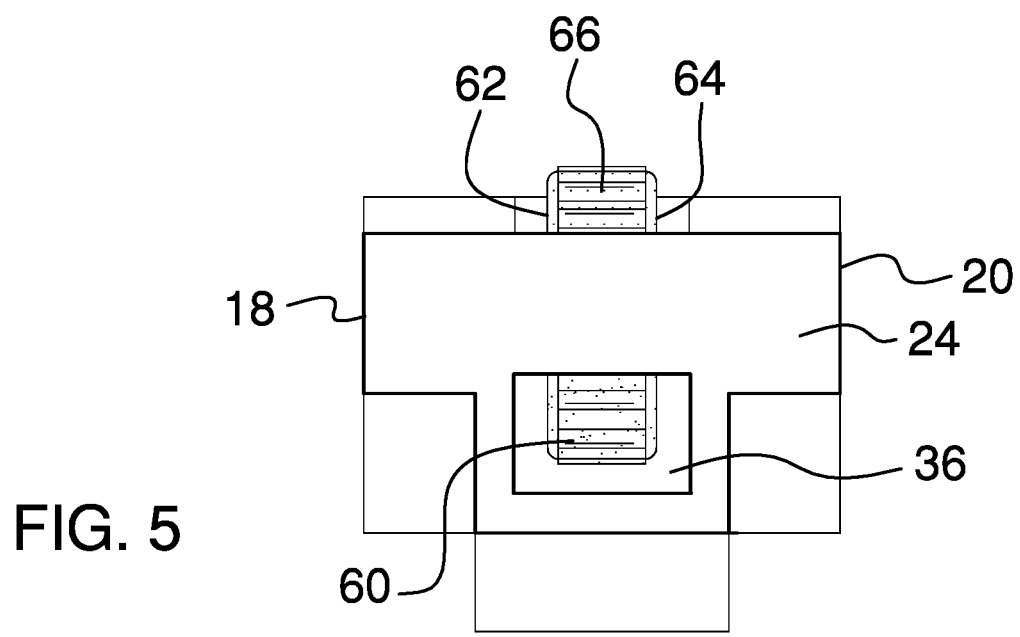
FIG. 5 is a rear elevation view of an embodiment of the disclosure.
Figure 6:
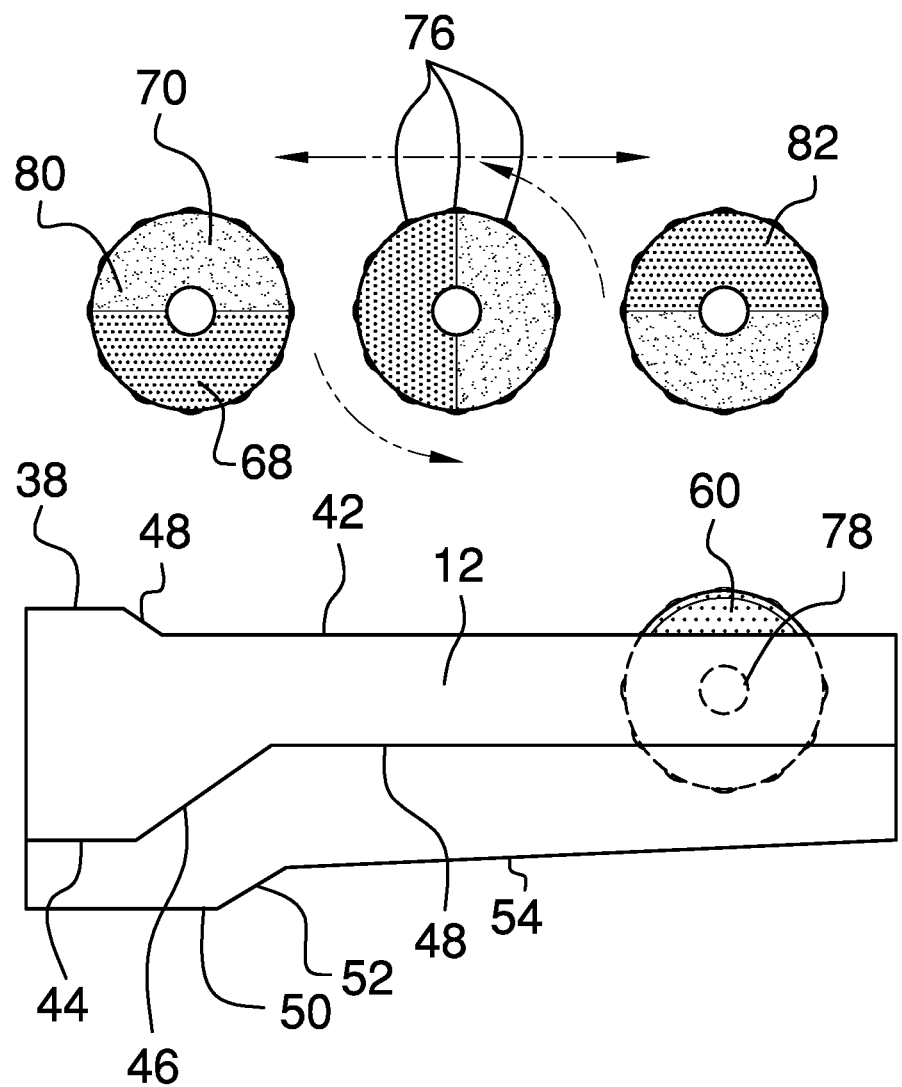
FIG. 6 is a side elevation view of an embodiment of the disclosure.
Figure 7:
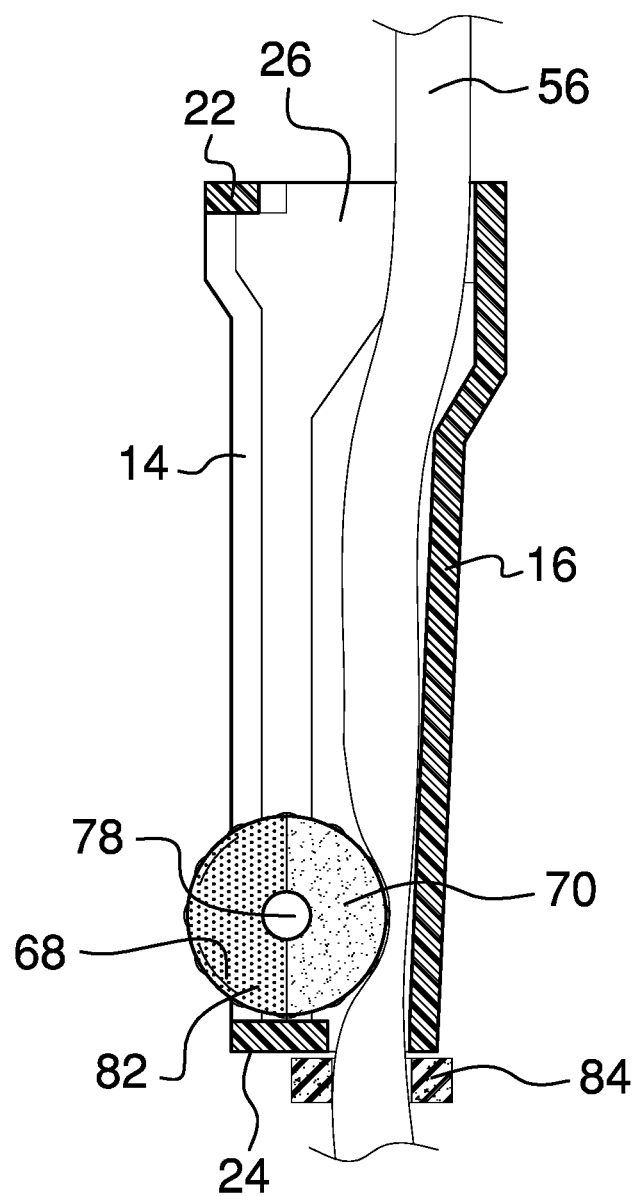
FIG. 7 is a cross-sectional view along line 6-6 of FIG. 1 an embodiment of the disclosure.

With reference now to the drawings, and in particular to FIGS. 1 through 7 thereof, a new tube clamp embodying the principles and concepts of an embodiment of the disclosure and generally designated by the reference numeral 10 will be described.

As best illustrated in FIGS. 1 through 7, the color-coded roller clamp apparatus 10 generally comprises a clamp housing 12 having a front side 14, a back side 16, a left side 18, a right side 20, a top side 22, and a bottom side 24 defining a clamp inside 26. A plus-shaped top aperture 28 extends through the top side 22 to the clamp inside 26. A roller slot 30 extends through the front side 14 to the clamp inside 16 from proximal the top side 22 to proximal the bottom side 24. The back side 16 has a raised medial portion 34 and a pair of lateral portions 32. The bottom side 24 has a bottom aperture 36 extending through the medial portion 32. The front side 14 has a flared top front portion 38 adjacent the top side 22, a ramped front portion 40 adjacent the top front portion 38, and a straight bottom front portion 42 extending to the bottom side 24. The lateral portions 32 of the back side 16 each have a flared top lateral portion 44 adjacent the top side 22, a ramped lateral portion 46 adjacent the top lateral portion 44, and a straight bottom lateral portion 48 extending to the bottom side 24. The medial portion 34 of the back side 16 has a flared top medial portion 50 adjacent the top side 22, a ramped medial portion 52 adjacent the top medial portion 50, and an angled bottom medial portion 54 extending to, and angling down towards, the bottom side 24.

The clamp housing 12 is configured to receive an IV tube 56 passing through the top aperture 28 and out the bottom aperture 36 along the medial portion 34. A roller 58 is coupled to the clamp housing 12 comprising a wheel 60 having a left face 62, a right face 64, and a perimeter face 66. The flared top front portion 38 of the housing 12 allows the roller 58 to move out of the way to insert or remove the IV tube 56. Each of the left face 62 and the right face 64 is chamfered adjacent the perimeter Ike 66, The wheel 60 partially extends through the roller slot 30. A first hemisphere 68 and a second hemisphere 70 of each of the left face 62, the right face 64, and the perimeter face 66 is a first color and a second color, respectively. A plurality of ribs 76 is coupled to the wheel 60. The plurality of ribs 76 is coupled to the perimeter face 66. The plurality of ribs 76 may be rounded and evenly spaced. The plurality of ribs 76 add grip to better pinch the IV tube 56. An axle 78 is coupled to the wheel 60 and centrally extends through each of the left face 62 and the right face 64. The axle 78 is coupled within the clamp inside 26 between the front side 14 and the pair of lateral portions 32 of the back side 16.

The roller 58 is rollingly moveable between a disengaged position 80 proximal the top side 22 and an alternative engaged position 82 proximal the bottom side 24. The wheel 60 in the disengaged position 80 exposes the first hemisphere 68 through the roller slot 30 and the wheel 60 in the engaged position 82 exposes the second hemisphere 70 through the roller slot 30 and is configured to clamp the IV tube 56 against the back side 16 to prevent flow. An annular stopper 84 is elasticized and configured to fit onto the IV tube 56 to support the bottom side 24 of the clamp housing 12.

In use, the user moves the roller 58 between the disengaged position 80 and the engaged position 82 to expose the first hemisphere 68 as a first color and a second hemisphere 70 as a second color through the roller slot 30. The first color and second color allow the user to more easily see if contents are moving through the IV tube 56.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A color-coded roller clamp apparatus comprising:
   a clamp housing, the clamp housing having a front side, a back side, a left side, a right side, a top side, and a bottom side defining a clamp inside, a top aperture extending through the top side to the clamp inside, a roller slot extending through the front side to the clamp inside from proximal the top side to proximal the bottom side, the back side having a raised medial portion and a pair of lateral portions, the bottom side having a bottom aperture extending through the medial portion, the clamp housing being configured to receive an IV tube passing through the top aperture and out the bottom aperture along the medial portion; and
   a roller coupled to the clamp housing, the roller comprising:
      a wheel, the wheel having a left face, a right face, and a perimeter face, the wheel partially extending through the roller slot, a first hemisphere and a second hemisphere of each of the left face, the right face, and the perimeter face being a first color and a second color wherein there is a distinct transition between the first color and the second color, respectively; and
      an axle coupled to the wheel, the axle centrally extending through each of the left face and the right face, the axle being coupled within the clamp inside between the front side and the pair of lateral portions of the back side, the roller being rollingly moveable between a disengaged position proximal the top side and an alternative engaged position proximal the bottom side, the wheel in the disengaged position exposing the first hemisphere through the roller slot and the wheel in the engaged position exposing the second hemisphere through the roller slot and being configured to clamp the IV tube against the back side to prevent flow.

2. The color-coded roller clamp apparatus of claim 1 further comprising each of the left face and the right face being chamfered adjacent the perimeter face.

3. The color-coded roller clamp apparatus of claim 1 further comprising a plurality of ribs coupled to the wheel, the plurality of ribs being coupled to the perimeter face.

4. The color-coded roller clamp apparatus of claim 1 further comprising the medial portion of the back side angling towards the front side from the top side to the bottom side.

5. The color-coded roller clamp apparatus of claim 1 further comprising the front side having a flared top front portion adjacent the top side, a ramped front portion adjacent the top front portion, and a straight bottom front portion extending to the bottom side, the lateral portions of the back side each having a flared top lateral portion adjacent the top side, a ramped lateral portion adjacent the top lateral portion, and a straight bottom lateral portion extending to the bottom side, the medial portion of the back side having a flared top medial portion adjacent the top side, a ramped medial portion adjacent the top medial portion, and an angled bottom medial portion extending to, and angling down towards, the bottom side.

6. The color-coded roller clamp apparatus of claim 5 further comprising the top aperture being plus-shaped.

7. The color-coded roller clamp apparatus of claim 1 further comprising an annular stopper, the stopper being elasticized and configured to fit onto the tube to support the bottom side of the clamp housing.

8. A color-coded roller clamp apparatus comprising:

a clamp housing, the clamp housing having a front side, a back side, a left side, a right side, a top side, and a bottom side defining a clamp inside, a plus-shaped top aperture extending through the top side to the clamp inside, a roller slot extending through the front side to the clamp inside from proximal the top side to proximal the bottom side, the back side having a raised medial portion and a pair of lateral portions, the bottom side having a bottom aperture extending through the medial portion, the front side having a flared top front portion adjacent the top side, a ramped front portion adjacent the top front portion, and a straight bottom front portion extending to the bottom side, the lateral portions of the back side each having a flared top lateral portion adjacent the top side, a ramped lateral portion adjacent the top lateral portion, and a straight bottom lateral portion extending to the bottom side, the medial portion of the back side having a flared top medial portion adjacent the top side, a ramped medial portion adjacent the top medial portion, and an angled bottom medial portion extending to, and angling down towards, the bottom side, the clamp housing being configured to receive an IV tube passing through the top aperture and out the bottom aperture along the medial portion;

a roller coupled to the clamp housing, the roller comprising:

a wheel, the wheel having a left face, a right face, and a perimeter face, each of the left face and the right face being chamfered adjacent the perimeter face, the wheel partially extending through the roller slot, a first hemisphere and a second hemisphere of each of the left face, the right face, and the perimeter face being a first color and a second color, respectively, wherein there is a distinct transition between the first color and the second color;

a plurality of ribs coupled to the wheel, the plurality of ribs being coupled to the perimeter face; and an axle coupled to the wheel, the axle centrally extending through each of the left face and the right face, the axle being coupled within the clamp inside between the front side and the pair of lateral portions of the back side, the roller being rollingly moveable between a disengaged position proximal the top side and an alternative engaged position proximal the bottom side, the wheel in the disengaged position exposing the first hemisphere through the roller slot and the wheel in the engaged position exposing the second hemisphere through the roller slot and being configured to clamp the IV tube against the back side to prevent flow; and an annular stopper, the stopper being elasticized and configured to fit onto the IV tube to support the bottom side of the clamp housing.

* * * * *